United States Patent
Sandell et al.

(10) Patent No.: US 6,610,509 B1
(45) Date of Patent: Aug. 26, 2003

(54) METHODS OF TARGETED EXPRESSION BY THE CD-RAP GENE PROMOTER

(75) Inventors: Linda J. Sandell, St. Louis, MO (US); Wei-Fen Xie, St. Louis, MO (US)

(73) Assignee: Barnes-Jewish Hospital, St. Louis, MO (US)

(*) Notice: Subject to any disclaimer, the term of this patent is extended or adjusted under 35 U.S.C. 154(b) by 0 days.

(21) Appl. No.: 09/360,394

(22) Filed: Jul. 23, 1999

Related U.S. Application Data

(60) Provisional application No. 60/094,092, filed on Jul. 24, 1998, and provisional application No. 60/094,861, filed on Jul. 31, 1998.

(51) Int. Cl.[7] .................. C12N 15/00; C12N 15/63; C07H 21/02; C07H 21/04

(52) U.S. Cl. .................. 435/69.1; 435/320.1; 536/23.1; 536/24.1

(58) Field of Search .................. 435/320.1, 69.1, 435/325; 536/23.4, 23.5, 24.1, 23.1

(56) References Cited

U.S. PATENT DOCUMENTS 6,143,878 A * 11/2000 Koopman et al. ......... 536/23.1

FOREIGN PATENT DOCUMENTS

EP 0854152 7/1998

OTHER PUBLICATIONS

Gerdes H et al. FEBS Letters 389:44–47, 1996.*
Bell, Donald M. et al. 1997. SOX9 directly regulates the type–II collagen gene. Nat. Genet. 16:174–78.
Blesch, A. et al. 1994. Cloning of a Novel Malignant Melanoma–derived Growth–Regulatory Protein, MIA. Cancer Res. 54:5695–5701.
Bosserhoff, Anja–Katrin, et al. 1996. Structure and Promoter Analysis of the Gene Encoding the Human Melanoma–inhibiting Protein MIA. J. Biol. Chem. 271:490–495.
Bosserhoff, Anja–Katrin, et al. 1997. Mouse CD–RAP/MIA Gene: Structure, Chromosomal Localization, and Expression in Cartilage and Chondrosarcoma. Developmental Dynamics, 208:516–525.
Bosserhoff, Anja–Katrin, et al. 1997. Function of MIA in metastasis of malignant melanoma. Proceedings of the American Association for Cancer Research. 38:290. Abstract.
Bosserhoff, Anja–Katrin, et al. 1997. Melanoma–inhibiting Activity, a Novel Serum Marker for Progression of Malignant Melanoma. Cancer Res. 57:3149–3153.
Bridgewater, Laura Clarke, et al. 1998. Chondrocyte–specific Enhancer Elements in the Col11a2 Gene Resemble the Col2a1 Tissue–specific Enhancer, J. Biol. Chem. 273:14998–15006.
Chansky, H.A., et al. 1997. Expression of a Cartilage–Derived Retinoic Acid–Sensitive Protein (CD–RAP) by Chondroid Tumors. 43rd Annual Meeting, Orthopaedic Research Society, p. 298–50.
Dietz, Uwe H. and Sandell, Linda J. 1996. Cloning of a Retinoic Acid sensitive mRNA Expressed in Cartilage and during Chondrogenesis. J. Biol. Chem. 271:3311–3316.

(List continued on next page.)

Primary Examiner—Ram R. Shukla
(74) Attorney, Agent, or Firm—Sonnenschein Nath & Rosenthal

(57) ABSTRACT

Provided are methods of targeted expression by the cartilage–derived retinoic acid–sensitive protein (CD-RAP) promoter. It is also directed to nucleic acid constructs and vectors useful for expression of nucleic acid sequences targeted to cartilage during development or in adult cartilage tissue, or for their expression in specific tumor cells such as chondrosarcomas and mammary tumor cells. The invention also relates to transgenic animals altered to contain the CD-RAP promoter transgene.

22 Claims, 8 Drawing Sheets

OTHER PUBLICATIONS

Figure 2A:
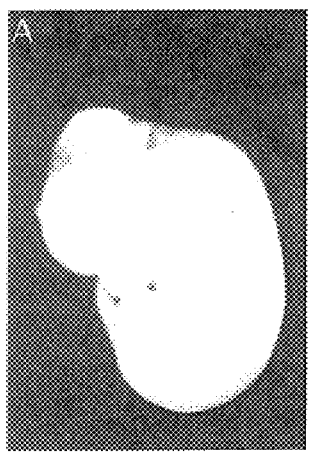

Ducy, Patricia, et al. 1997. Osf2/Cbfa1: a Transcriptional Activator of Osteoblast Differentiation. Cell 89: 747–754.

Foster, Jamie W., et al. 1994. Campomelic dysplasia and autosomal sex reversal caused by mutations in an SRY–related gene. Nature 372: 525–530.

Grossschedl, Rudolf, et al. 1994. HMG domain proteins: architectural elements in the assembly of nucleoprotein structures. Trends Genet. 10: 94–100.

Horton, W., et al. 1987. Identification of a phenotype–specific enhancer in the first intron of the rat collagen II gene. Proc. Natl. Acad. Sci USA 84: 8864–8868.

Kondo, S., et al. 1998. IGF–1 Up–Regulates CD–RAP Gene Expression Through an AP–2 Binding Site. 44th Annual Meeting, Orthopaedic Research Society. p. 178–30.

Kondo, S., et al. 1998. Regulation and Function of CD–RAP, a New Cartliage–Specific Protein. Orthop. Trans. 21:848.

Lefebvre, Veronique, et al. 1997. SOX9 is a Potent Activiator of the Chondrocyte Specific Enhancer of the Proα1 (II) Collagen Gene. Mol. Cell. Biol. 17:2336–2346.

Lefebvre, Veronique, et al. 1998. Toward Understanding SOX9 Function in Chondrocyte Differentiation. Matrix Biol. 16: 529–540.

Lu, Junxuan, et al. 1997. Gene Expression Changes Associated With Chemically Induced Rat Mammary Carcinogenesis. Mol. Carcinogenesis 20: 204–215.

Ng, Ling–Jim, et al. 1997. SOX9 Binds DNA, Activiates Transcription, and Coexpresses with Type II Collagen during Chondrogenesis in the Mouse. Dev. Biol. 183: 1080–121.

Ryan, Maureen C., et al. 1990. The Human Type II Procollagen Gene: Identification of an Additional Protein–Coding Domain and Location of Potential Regulatory Sequences in the Promoter and First Intron. Genomics 8: 41–48.

Sandell, Linda J., et al. 1991. Alternatively Spliced Type II Procollagen mRNAs Define Distinct Populations of Cells during Vertebral Development: Differential Expression of the Amino–Propeptide. J. Cell Biol. 114: 1307–1319.

Sandell, Linda J., et al. 1994. Alternative Splice Form of type II Procollagen mRNA (IIA) Is Predominant in Skeltal Precursors and Non–Cartilaginous Tissues During Early Mouse Development. Dev. Dyn. 199: 129–140.

Schorle, Hubert, et al. 1996. Transcription factor AP–2 essential for cranial closure and craniofacial development. Nature 381: 235–238.

Sudbeck, Peter, et al. 1996. Sex reversal by loss of the C–terminal transactivation domain of human SOX9. Nat. Genet. 13: 230–232.

van Groningen, Jan J.M., et al. 1995. Identification of Melanoma Inhibitory Activity and Other Differentially Expressed Messenger RNAs in Human Melanoma Cell Lines with Different Metastatic Capacity by Messenger RNA Differential Display. Cancer Res. 55: 6237–6243.

Wright, Edwina, et al. 1995. The Sry–related gene Sox9 is expressed during chondrogenesis in mouse embryos. Nat. Genet. 9: 15–20.

Xie, Wei–Fen, et al. 1998. Regulation of the Mouse Cartilage–derived Retinoic Acid–sensitive Protein Gene by the Transcription Factor AP–2. J. Biol. Chem. 273:5026–5032.

Xie, Wei–Fen, et al. 1998. Mouse CD–RAP Promoter Directs Cartilage–Specific Expression in Vivo. 44th Annual Meeting, Orthopaedic Research Society. pp. 207–235.

Zhang, Jian, et al. 1996. Neural tube, skeletal and body wall defects in mice lacking transcription factor AP–2. Nature 381: 238–241.

Zhao, Qi, et al. 1997. Parallel Expression of *Sox9* and *Col2a1* in Cells Undergoing Chondrogenesis. Dev. Dyn. 209: 377–386.

Zhou, Guang, et al. 1998. Three High Mobility Group–like Sequences within a 48–Base Pair Enhancer of the *Col2a1* Gene Are Required for Cartilage–specific Expression in Vivo. J. Biol. Chem. 273: 14989–14997.

* cited by examiner

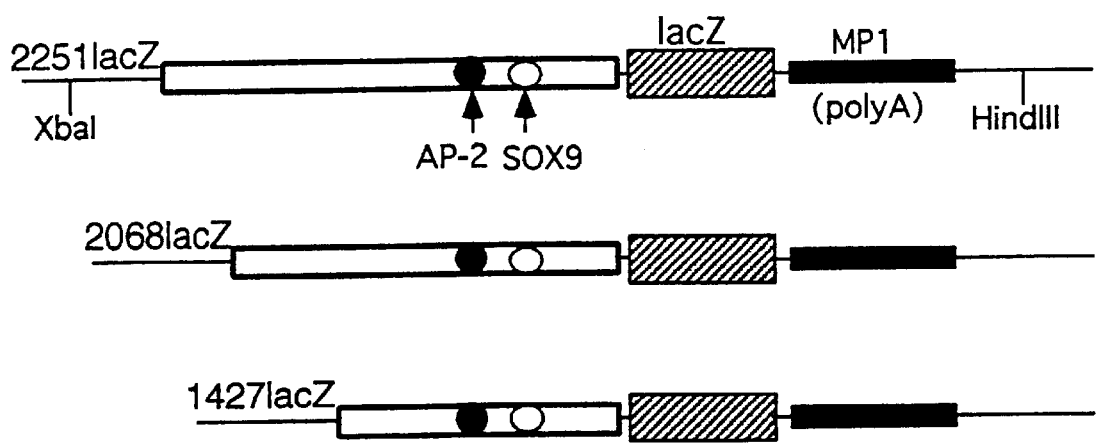
F/G./

FIG. 6

```
CCAAGGAGTCTACCAATAGAGCTACATTTAGTCCCCTATGTATTAGTTAG
TTGTCTCCCAGAGGCCTTCAGATTTTCATGCCTTGAATCTTCACAGTGCC
AAGATTTGAAACTAGTATTTACAGTAAAATATCTACTGCCCAAAGAAACA
                    NF-IL6
CTTTGATGTATTCTAAATTGGGAAATTCAAAACATGAGAACAACATGCTA
CCTCATGGTCTCTGCTACCAGCTTCATTTATTTACCAACTTGTGTCTAAA
           PEA3
ACTTCTCAAGGAAATCACCTCCTACACTTATTTTACAGTGGTCTTACTGT
TTTAGTTTTTGTGGTTCTGGGCATTGAACCCAGGGCTTTGTACATACTAG
ACAAAGCTCAGTCCTGGGCCCCTGACATATATTTTAGTTATAAATTATCA
TACATTATTTTTTGGCTTGGGAATTGAACCCAAGATTATCAGGCATTCAA
CCACTATGTTCCTGTCCTGTTGCTATGAAGAGACACCAGAACTAAAGTAA
ATTAAAGGCAGAGCATTTACTAGAGGTCTTGCTTATAGTTGAAGAGAATC
AGTTCGTGGTGATTATGACAGCATGGCAGCAGGCAGGCATGATGCCAAAG
                                         αINF-2
CAATAGCTGAGAGCTTAAACCTGGCAAAGATGAGGCAGTGAAAGGAGAG
PEA3
GAAATGTGTGGGGGTGTGGTGGGGGGTCTGGCTTGGACTTTTTTTTTCAT
TAAAAAATTTTTTATTAGATATTTTCTTTATTTACATTTTAAATATTATC
   ICSbf             Pyr-rich
CCCTTTCCTAGTTTCCCCTCTGAAAATCCCCTCTCCCCTCCCCATGGCT
            W-element
TGAGCTTTTTGAAACTTAAAAGCTCACACCCAGTGACAGAACTCTACCAAC
     bHLH
AAGGTCATCTGCCAACCTTCCTAAACAGTTCCACCTACTGGGAACCAAAC
ATTCACATATACTAGCCTATTGGGACCACCTTATTCAAACTATAACCATT
AAGCTATAGTTTCAGCCTCAGTCTGTTGATTGCATCCTTGTGAGGTCACT
AAACATGCTCTTTGGGCCTCTGTTCCTTGCACGTCTGTTCATGGACTGCT
                                     GATA-1
CCTTCTAAGAGGCATGTCAGGTCAGATAACAGTGATACTAAGAAACCCTG
AT-rich                        c-Myb
AAATAAATCTTTTTTCCCCTTCCTGGTTCAGTTACCATAGACATACATT
                                                C/EBP
CTTTAGCTCAATTTCTTTGTGAACTGGGCTTGTCAGGGCTACTCCTGAGG
and NF-IL6                                      bHLH
CAATTCAGACCATCCCTGATATATACATATATGATTTTTACACATGCATA
TATATGTATGTGTATATATACATACATACATATATATAGTATATACACAT
                              bHLH
ATATATTTTGTGTGGGTGTACATACACACACATGCATATGATTTGCTGGT
         NF-IL6
GCATGCCTTACCCACGTTTGGAAAGGCAGAGGCAGGTTGATCTCTTAAGA
                    NFKB
GTTTGAGGCCAGTCTGGTCTTTATAGGGAGTTCCAGGCCAGCCAGGGCTG
TGCAGTAGTAGATCGGTGTCTCAAGAAAAAAGAGTGGGCTGGAAAGATGG
                                bHLH
CTCAGCGGTTAAGAGCAGAGCACGAGTGGGTCTTCCAGATGACCCAGGTT
TGATTCCTAGCACCTAGCTCTGTAGCTCCAGTTCCAGAAGACTCAAGACC
                                bHLH
CTCTTCTGGCCTTTAAAAATACCAGGCACACATGCAGTACTCAGACATAC
bHLH/c-Myb
ATGCAGCAGTTGTTTGCTTTCATTGCTTTCTTTATAGATGAGTGGGTTGA
                                      PEA3/TCF-2-α
AGCTCATAAGCTAGAATAGCTTAGCTTCTAGTGAGGAAGTAAGCCTGTA
          ZESTE bHLH
ATGTGCACAGTGAGCCAGGTGGGACAGTGCCTAGCCTGAGGCCAGACGTT
                W-element
GAGTGTTTGCTCAGTACCTGGGAACCCTGGCTGTGGCTGCTAATCAAAGA
                                   PEA3
ACTGCCTTGTTCCAGACCTCAGCACAGGAAATTCCAGGGTGGTTTTCTA
                     GATA-1
TACTGGCTCCTCTAGCTTGGTCTCTGGAGGGTCCAGGTACCTAAAACGAC
TTGAAGGTGGAATCAGATAGTCCAGCCTGCCTATCTGCGTCTCTAGTTAT
CCAGGGGGTGATCGCTACTTGGAATTGCCTGAATTGCTTTGGGCTCGAGT
```

```
AGGCATTTTCTTTGGCCCATAGCCCTTACCCTCTCTCTAAAATGGTACTG
                                          Sp1
GCTGGAGAACAACCTTGGGGAGTGGGTGAGGGTGAAATTTGGTTTGGGGC
GGAGACAGGATCGAGAACACAGGTTTCCTTGATATTCAGCCTGGAAGGAG
                            bHLH
GGCAGGAGGAGCCCAGAGACCTCGTTCTTCACTTGGTCATTCTCAGTCCA
+1
TGATGGTGTGGTCCCCAGTGCTCCTTGGCATCGTCGTCTTGTCTGTTTTT
 M  V  W  S  P  V  L  L  G  I  V  V  L  S  V  F
TCAGGGCCTAGCAGGGCTGATCGAGCTATGCCCAAGCTGGCTGACTGGAA
 S  G  P  S  R  A  D  R  A  M  P  K  L  A  D  W  K
GCTGTGTGCGGACGAGGAATGCAGCCgtaagagtcagggaacaagggaag
 L  C  A  D  E  E  C  S
ggggctgaaggcttggactgctagtctgttttgcagttgctgtcatttcc
ttctccctccccagATCCTATCTCCATGGCTGTGGCCCTCCAGGACTACG
                H  P  I  S  M  A  V  A  L  Q  D  Y
TGGCCCCTGATTGCCGCTTCTTGACTATATAGGGGCCAAGTGGTGTAT
 V  A  P  D  C  R  F  L  T  I  Y  R  G  Q  V  V  Y
GTCTTCTCCAAGTTGAAGGGCCGTGGGCGCCTTTTCTGGGGAGGCAGTgt
 V  F  S  K  L  K  G  R  G  R  L  F  W  G  G  S
gagtcttcaaaaagtgataatgggaagggtgtggggttttgtttgggttttg
taaagcctttgttttccatatgaagggaagattttggggggagggggaaaacg
agatttgggggaaggaaggacatttttattacttattgcatttttttttt
ttcttttagaaattacagagaagcttagcgccaaagctcttttcatacccc
gggatacaacagtgaacaaagggtagaggcaggcaaccagcaagccatc
aaaagtggcagcaaacatgacattgtgaggattagttgtagtggcaacat
tctatccatgagcaaatggcatttaagctgagattcaagtaagagggaag
attgtacacaggcgttcagcaagcataagtgccgtttcccccagatggact
tttaacttcttctccagGTTCAGGGAGGTTACTATGGAGACCTGGCAGCC
                   V  Q  G  G  Y  Y  G  D  L  A  A
CGGCCTGGGCTATTTCCCCAGTAGCATTGTCCGGGAGGACCTGACTCTGAA
 R  L  G  Y  F  P  S  S  I  V  R  E  D  L  T  L  K
ACCTGGCAAAATTGATATGAAGACCGATgtgagtgtcttggggggtggagg
 P  G  K  I  D  M  K  T  D
tgggagtaggatgatagtcctttatttgcttaccctgtttatgagaagta
attattttttgttgttggtatgtacccaagctggcctcaaaatcactagcc
tccagtttcagcctcctgagggctgctgagtttacaggccctgcccagtg
ctgagtgatctctaattgggaaatggcagagggtgcagtactggaagcta
atgtgttcatttctgggtgatcaaacctagtccttgcagctataactttg
ttagaaccactaggcgcattgcaatgtcatcactggttggttttctattt
actcttttttcagCAATGGGATTTCTACTGCCAGTGAGCTCAGCCTACCGC
               Q  W  D  F  Y  C  Q  *
TATCCCTGCAGTTACCCTTCCGGCTCTATGCAAATACAGCAGCCAATGGC
AAACTATTTGTCTCTTTGGTTTTTGGGGTTGGGTGGGTATNTGCAAANAA
TGTTTCACGGGTTTCTGAATATANCCAATTAATGCCCTGAATGTTGTAAC
GTCAGTGGCTACTAGGCAAAATTTCACTTTGCAAGCCCTTTGCTCCAAGG
TAAGGTTTGGGACCCCCAAGCAAGGGGGTAAACAGTACAATATATGTACG
CTTTCCTCTCTTTTAAAGGGAGTTGAATCATTGGTATGANCCAATAGATC
CCGANAAGCGCATAGAACGTNCAGTTTTTTT
```

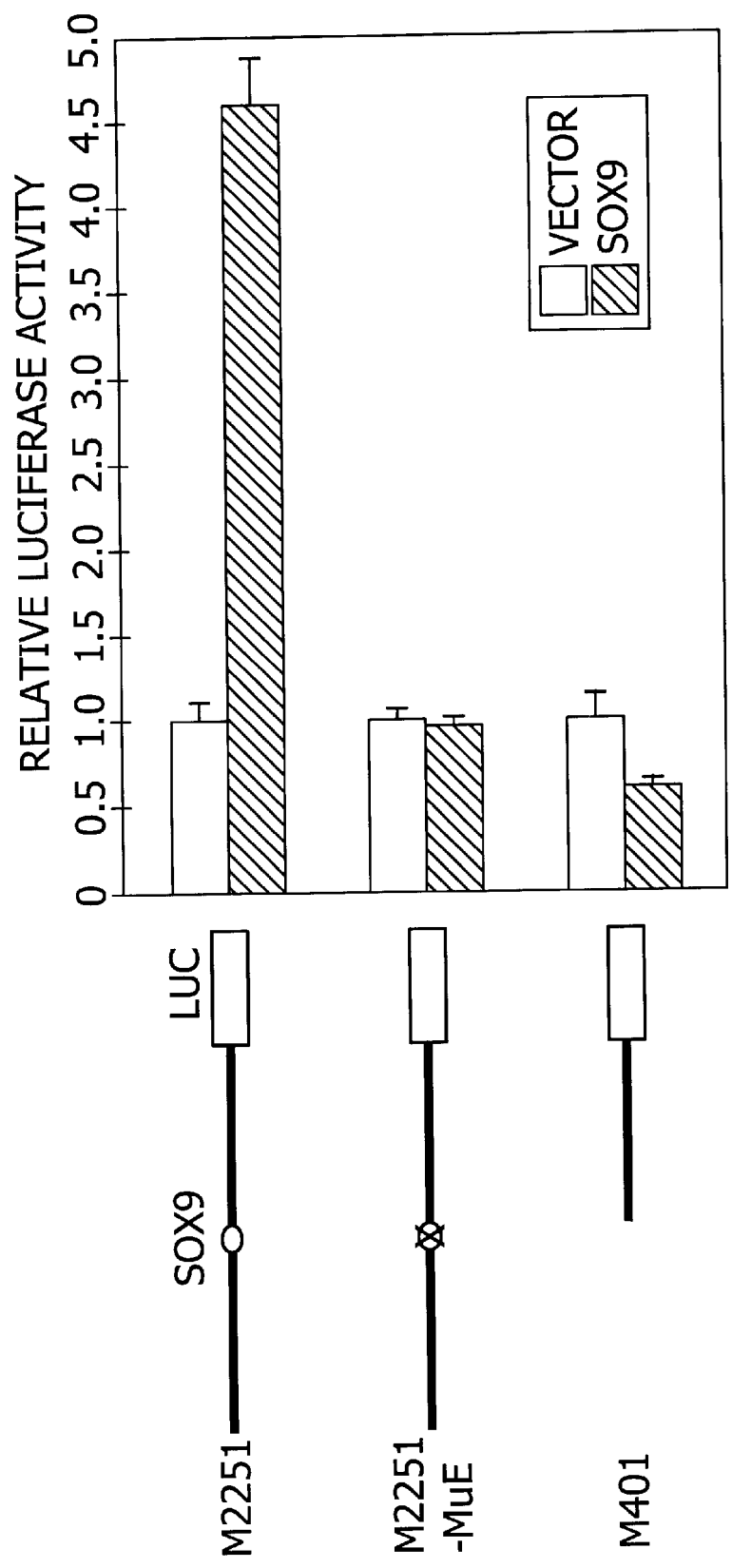
FIG. 7 ACTIVATION OF CD-RAP GENE BY Sox9

METHODS OF TARGETED EXPRESSION BY THE CD-RAP GENE PROMOTER

"This application claims the benefit of U.S. Provisional Application No. 60/094,092, filed Jul. 24, 1998 and U.S. Provisional Application No. 60/094,861, filed Jul. 31, 1998."

The contents of Applicants' provisional applications 60/094,861 and 60/094,092 are herein incorporated by reference.

This invention was developed with Government support under NIH grants R01AR36994 and R01AR45550. The Government has certain rights in,the invention.

BACKGROUND OF THE INVENTION

The present invention relates to methods of targeted expression by the cartilage-derived retinoic acid-sensitive protein (CD-RAP) promoter. It is also directed to nucleic acid constructs and vectors useful for expression of nucleic acid sequences targeted to cartilage during development or in adult cartilage tissue, or for their expression in specific tumor cells such as chondrosarcomas and mammary tumor cells. The invention also relates to transgenic mice and other animals altered to contain the CD-RAP promoter transgene.

Cartilage-derived retinoic acid-sensitive protein (CD-RAP) was identified from bovine chondrocytes by the techniques of reverse transcription-polymerase chain reaction (PCR) and differential display during the attempt to identify the molecular markers in the regulation of chondrogenesis (Dietz and Sandell, 1996). The protein was previously isolated and cloned as melanoma inhibitory activity (MIA) from a human melanoma cell line (Blesch et al., 1994). The entire gene encoding CD-RAP/MIA is well conserved among different species, including four exons which are interrupted by three introns (Dietz and Sandell, 1996; Bosserhoff et ,al., 1997a). Functional analysis of the CD-PAP/MIA promoter shows that this gene is actively expressed in the human and murine melanoma cells and its activity is inducible by phorbol ester (Bosserhoff et al., 1996). Unlike other cartilage genes such as collagen types II, IX, and XI, which are also observed in a variety of non-cartilaginous tissues during embryogenesis (Sandell et al., 1991; Cheah et al., 1991; Sandell et al., 1994; Yoshioka et al., 1995), the normal expression of CD-RAP/MIA is restricted to cartilage cells of the chondrocyte lineage and mature chondrocytes. With a more restricted expression pattern in normal tissues, CD-RAP has also proven to be a good model for the studies of the transcriptional regulation of cartilage specific genes. CD-RAP/MIA is activated during the beginning of chondrogenesis and expressed throughout cartilage development (Dietz and Sandell, 1996; Bosserhoff et al., 1997a). One exception to the exclusive expression in cartilage is the expression in premammary buds of the embryo.

So far, little is known about the function of CD-RAP/MIA in chondrogenesis. CD-RAP is coregulated by RA with type II collagen which is the most abundant extracellular protein made by chondrocytes and generally considered to be characteristic of cartilage, suggesting the potential role of CD-RAP in morphogenesis and differentiation of chondrocytes. RA is a potent morphogen in embryogenesis and fetal development and is involved in cartilage differentiation. Applicant's analysis of the CD-RAP transgene reveals that the CD-RAP expression is correlated with chondrogenesis. But its expression level is decreased in hypertrophic chondrocytes, implying that CD-RAP may be required for the maintenance of chondrocyte phenotype.

The function of CD-RAP/MIA in carcinogenesis and metastasis is also poorly understood. CD-RAP/MIA is detected at various levels in malignant melanoma, chondrosarcoma and mammary carcinomas (Blesch et al., 1994; van Groningen et al., 1995; Bosserhoff et al., 1997a and b; Lu et al., 1997). In primary chondrocytes, CD-RAP/MIA inhibits DNA synthesis (Kondo et al., 1998). Similarly, treatment of a melanoma cell line HTZ-19 with MIA resulted in inhibition of DNA synthesis and significant change of cell morphology as melanoma cells rounded up (Blesch et al., 1994). Evidence suggests that CD-RAP/MIA plays an important role in carcinogenesis and tumor metastasis as CD-RAP/MIA mediates the detachment of melanoma cells from extracellular matrix molecules (Bosserhoff et al., 1997c). Increased serum levels of CD-RAP/MIA were detected in 100% of the patients with metastatic melanoma. In contrast, none of the patients with negative CD-RAP/MIA values developed metastasis, suggesting that CD-RAP/MIA may participate in tumor invasion and metastasis (Bosserhoff et al., 1997b). The CD-RAP/MIA serum level is currently used for the staging and monitoring of metastatic melanoma (Bosserhoff et al., 1997b). CD-RAP/MIA serves as a novel serum marker for malignant melanoma with the highest sensitivity and specificity compared with S-100 and soluble intercellular adhesion molecule 1.

Analysis of CD-RAP transgenic mice demonstrates that CD-RAP is only expressed in mammary gland at very early stage of the development of mammary buds. But it is reexpressed in the chemically induced rat mammary carcinomas. Furthermore, sequence comparison of CD-RAP/MIA gene from malignant tumors with that from normal tissues reveals no mutation in the coding region (Lu et al., 1997). These results support the hypothesis that overexpression of CD-RAP/MIA rather than specific gene mutation may contribute to the carcinogenesis of breast cancer (Lu et al., 1997).

To better understand the functioning of genes, researchers have focused on transcription regulation, including the influence of transcription factors on promoters. Transcription factors, AP-2 and SOX9, have been shown to be important for chondrocyte differentiation (Foster et al., 1994; Wright et al., 1995; Schorle et al., 1996; Zhang et al., 1996; Ng et al., 1997; Zhao et al., 1997). CD-RAP is the first cartilage gene shown to be regulated by AP-2 (Xie et al., 1998). The importance of AP2 in chondrogenesis is demonstrated in AP-2 knock out mice which reveal severe skeletal deformation (Schorle et al., 1996; Zhang et al., 1996). Applicants have shown that AP-2 is biphasically involved in the regulation of CD-RAP promoter activity and response to retinoic acid (RA), specifically, applicants have demonstrated that transactivation by AP-2 contributes to the constitutively high expression of CD-RAP in chondrocytes and that the overexpression of AP-2 induced by RA results in significant reduction of the CD-RAP transcript (Xie et al., 1998).

In addition, SOX9 is able to activate the expression of several cartilage genes, including collagen types II and XI (Lefebvre et al., 1997; Bell et al., 1997; Zhou et al., 1998; Bridgewater et al., 1998). SOX9 protein contains a high mobility group (HMG)-type DNA binding domain and a transactivation domain which was mapped within the 100 C-terminal amino acids (Grosschedl et al., 1994; Sufdbeck et al., 1996). Haploinsufficiency of SOX9 has been attributed to the campomelic dysplasia, a skeletal malformation syndrome (Foster et al., 1994). SOX9 can bind to the CD-RAP promoter and enhances the CD-RAP expression. However, it appears that additional transcription factors are essential for the activation of chondrocyte differentiation, since neither SOX9 nor AP-2 is able to stimulate cartilage gene expression in nonchondrogenic cells (Lefebvre and de Crombrugghe, 1998; Xie and Sandell, unpublished data).

Because CD-RAP may play critical roles in chondrogenesis, carcinogenesis, and metastasis, deeper understanding of its transcriptional regulation, especially in specific tissues, can lead to effective design of therapeutic agents and diagnostics and research tools. Tissue specific gene expression in cartilage, as well as in tumor cells such as chondrosarcoma or mammary tumors is frequently desirable. For example, growth factors or enzymes could be targeted to cartilage tissue to enhance tissue regeneration or repair without affecting surrounding tissue. Similarly, drugs designed to inhibit tumor cell growth or antigenic proteins which can be used to trigger an immune response could thereby be selectively delivered to the tumor cells with minimal adverse impact on surrounding healthy tissue.

SUMMARY OF THE INVENTION

Among the objects of the invention, therefore, may be noted the provision of methods of targeting expression of desired nucleic acid sequences specifically to cartilage primordial cells and adult articular cartilage cells. Also provided is a means for expressing desired nucleic acid sequences specifically in chondrosarcoma or mammary tumor cells. Nucleic acid constructs and vectors for the introduction of the desired nucleic acid sequences and transgenic animals altered to express desired nucleic acid sequences in the above-mentioned specific tissue cells are also provided.

Thus, the present invention is directed to a method for the expression of a desired nucleic acid sequence in cartilage cells of the chondrocyte lineage or mature chondrocyte cells comprising the steps of transfecting the cells with a nucleotide construct containing a murine CD-RAP gene 5'-flanking segment capable of targeting such cells for expression operably linked to a nucleic acid sequence to be expressed and expressing the desired nucleic acid sequence. Methods employing these steps for targeted expression in chondrosarcoma or mammary tumor cells or cell lines derived therefrom are also provided.

The invention is further directed to a nucleotide construct comprising a murine CD-RAP gene 5'-flanking segment operably linked to a foreign nucleic acid sequence.

A further aspect of the present invention is directed to a nucleotide construct comprising a human CD-RAP gene 5'-flanking segment operably linked to a foreign nucleic acid sequence.

The invention also relates to application of a recombinant transcription factor, such as sox9, to alter expression of a CD-RAP promoter construct.

The present invention is also directed to a vector for expression of a desired nucleic acid sequence comprising a nucleotide construct containing a murine CD-RAP gene 5'-flanking segment and said nucleic acid sequence wherein said nucleic acid sequence is located in sequential and positional relationship for expression of the nucleic acid sequence.

A further aspect of the present invention is directed to a vector for expression of a desired nucleic acid sequence comprising a nucleotide construct containing a human CD-RAP gene 5'-flanking segment, a reporter sequence, and said nucleic acid sequence wherein said nucleic acid sequence is located in sequential and positional relationship for expression of the nucleic acid sequence.

The invention is additionally directed to a transgenic animal comprising such a nucleotide construct.

BRIEF DESCRIPTION OF DRAWINGS AND ABBREVIATIONS

Abbreviation
bp=base pair(s)
CD-RAP=cartilage-derived retinoic acid-sensitive protein
HMG=high mobility group
lacZ=the *Escherichia coli* β-galactosidase gene
MIA=melanoma inhibitory activity
p.c.=postconception
PCR=polymerase chain reaction
RA=retinoic acid
X-gal=5-bromo-4-chloro-3-indolyl-β-Dgalactopyranoside.

FIG. 1 is a chematic map of the constructs used for generation of transgenic mice of the invention. Three different lengths of the mouse CD-RAP promoter were linked to the *Esherichia coli* β-galactosidase gene (lacZ) followed by an intron and a polyadenylation signal (polyA) of murine protamine gene (solid box). The empty box represents the mouse CD-RAP promoter and the hatched box denotes the lacZ. The restriction sites used for releasing the constructs and the binding sites for transcription factors AP-2 (solid circle) and SOX9 (empty circle) are also shown.

FIGS. 2A–E depicts the expression of 2251lacZ in transgenic embryos at different stages of development. The embryos were collected by Cesarean section at days 11.5(A), 12.5(B), 13.5(C), 15.5(D), and 16.5(E) of gestation and whole mount-stained with X-gal. The β-galactosidase activity was observed in the mammary gland primordium (arrow) and cartilage.

Figure 3A:
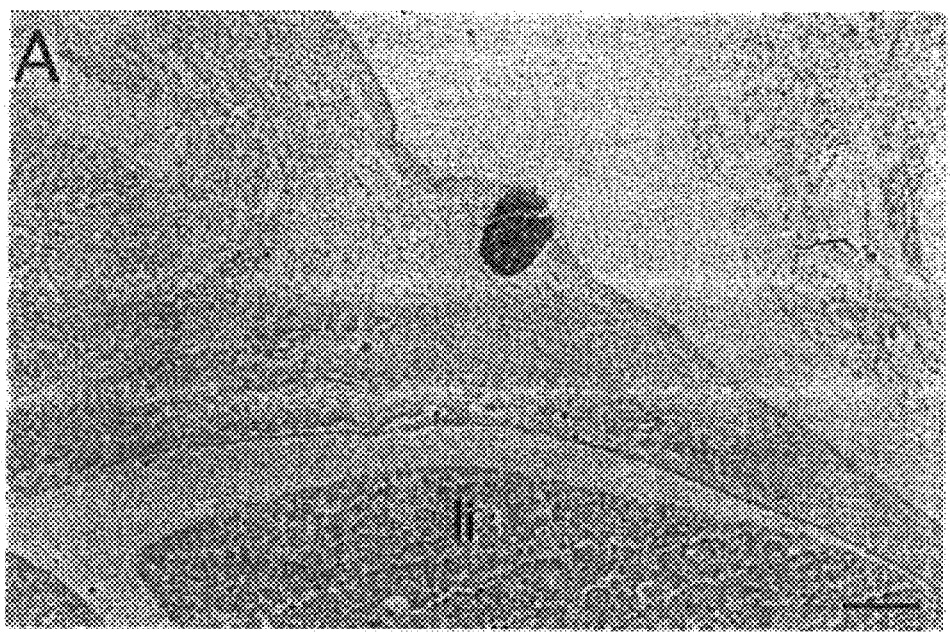
Figure 3B:
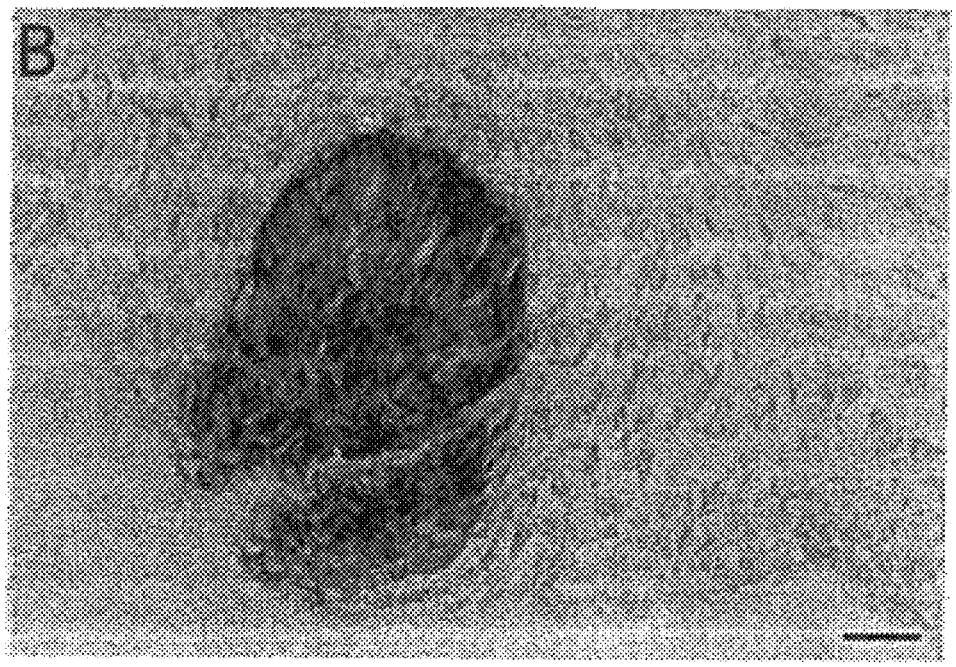

FIGS. 3A–B depicts the transgene expression in mammary buds. The blue X-gal reaction products were detected in the epithelial cells. No staining was detected in liver (li). A, bar=200 μm. B, bar=20 μm.

Figure 4A:
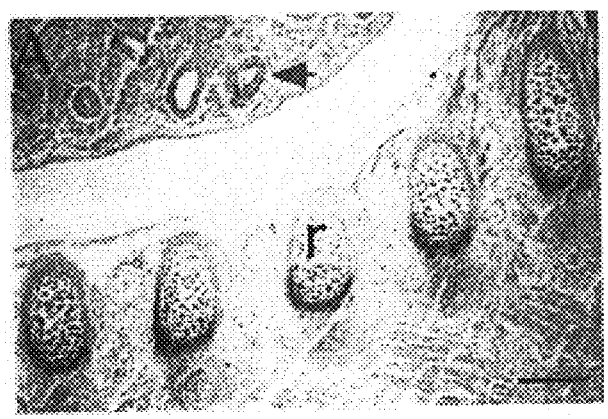
Figure 4B:
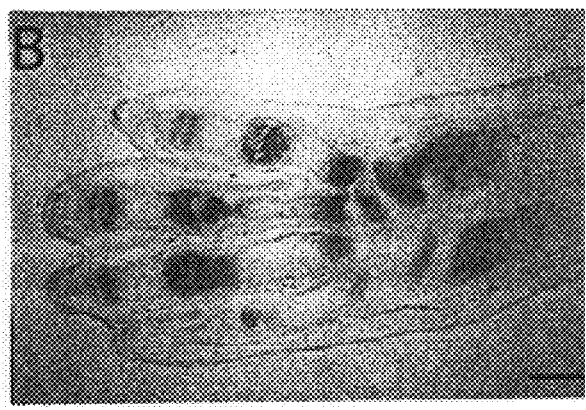
Figure 4C:
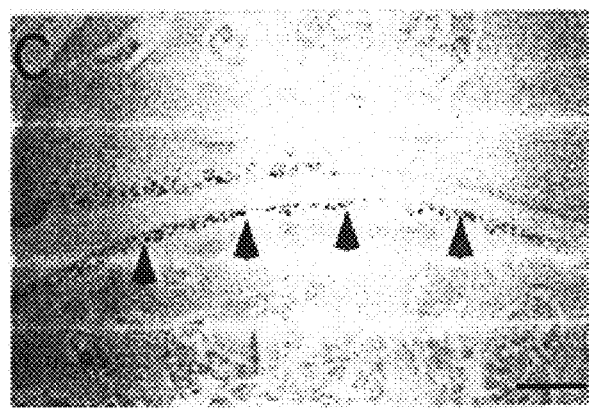

FIG. 4 represents a histological analysis of transgene 2251lacZ expression. FIG. 4A is the expression of the lacZ constructs in cartilage. X-gal staining was positive in the chondrocytes of rib (r) and cartilaginous lung bronchi (arrow) from a 13.5-day p.c. embryo. FIG. 4B is a section of the forelimb at day 15.5 p.c. The β-galactosidase activity was located in proliferation chondrocytes. Transgene expression in hypertrophic chondrocytes decreased. In FIG. 4C, transgene expression in an adult animal is depicted. LacZ expression was observed in the cartilage surface from an 8-week knee joint section (arrow). Bars: (A and C) 100 μm; (B) 200 μm.

Figure 5:
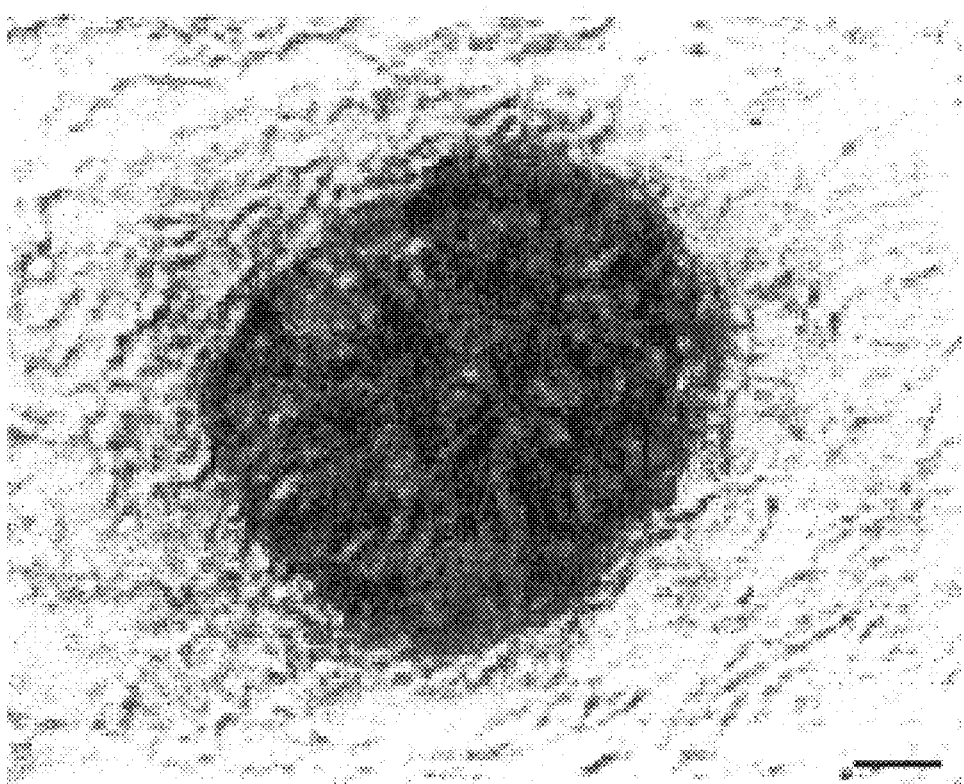

FIG. 5 depicts the immunolocalization of CD-RAP in mammary gland. A 13.5-day p.c. embryo was stained with X-gal overnight to reveal the mammary gland and then was sliced on a microtome. Immunohistochemistry was carried out as described below in the examples. The blue color represents the X-gal reaction products. Immunostaining is indicated by the red color products in the cytoplasm of epithelial cells. Bar=20 μm.

FIG. 6 (SEQ ID NO 1) depicts the complete nucleic acid sequence of a murine CD-RAP gene. In addition to the nucleic acid sequence, the figure shows the location of various cis-acting elements.

FIG. 7 shows the induced expression of a CD-RAP promoter construct by sox9. Sox9 expression plasmid is cotransfected with each of three different constructs into a rat chondrosarcoma cell line. The first construct includes a reporter gene encoding luciferase and a CD-RAP 5'-flanking segment containing the sox9 consensus sequence. The second construct consists essentially of the first construct, except the sox9 consensus sequence has been mutated by site-directed mutagenesis. The third construct contains the reporter gene, but lacks the sox9 consensus sequence. Where sox9 is able to bind to the sox consensus sequence, i.e. to the wild-type sox consensus sequence, CD-RAP promoter activity increases, as measured by the increased expression of luciferase.

Figure 8:
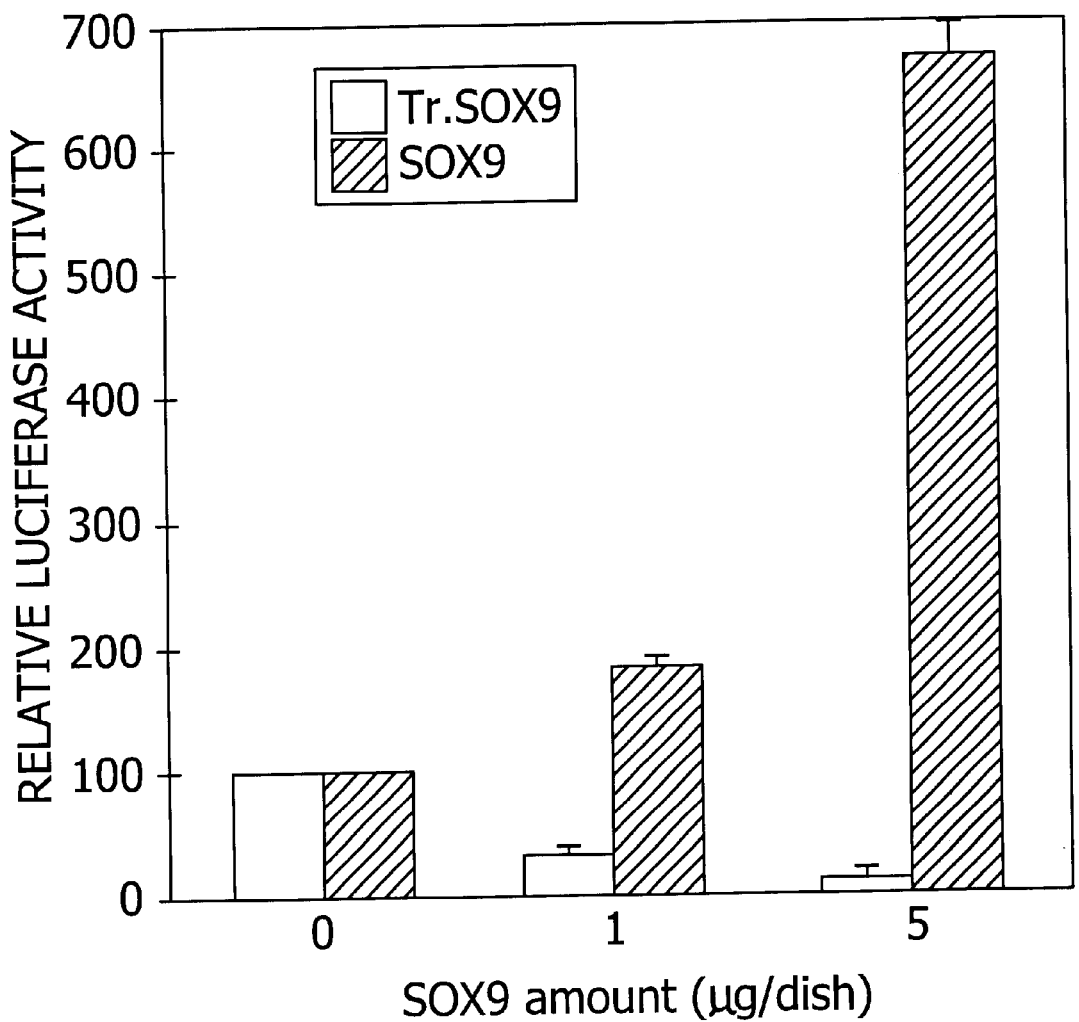

FIG. 8 is a depiction of the inhibition of CD-RAP promoter activity by a truncated sox9. A construct comprising a CD-RAP 5'-flanking segment and a reporter gene is cotransfected with a wild-type sox9 or a truncated sox9. The host is a rat chondrosarcoma cell line. With increasing amounts of wild-type sox9, CD-RAP promoter activity increases. With increasing amounts of truncated sox9, on the other hand, CD-RAP promoter activity is inhibited.

DETAILED DESCRIPTION OF THE PREFERRED EMBODIMENTS

The contents of each of the reference cited herein are herein incorporated by reference.

Definitions

A "cis-acting element" refers to a gene which regulates transcription of nearby genes on the same chromosome by binding transcription factors.

A "construct", as used herein, refers to a nucleotide cassette comprising a foreign nucleic acid of interest covalently linked to a vector. The construct may include a reporter gene and/or a tag.

A "vector" means a piece of nucleic acid capable of carrying and transmitting a foreign nucleic acid to a target cell, tissue, or animal.

A "reporter gene" refers to any gene capable of providing a signal for the intended purpose. For example, a luciferase reporter can provide a means to follow the CD-RAP promoter activity; increased luciferase activity corresponds to increased CD-RAP promoter activity. Furthermore, a reporter gene may be an antibiotic-resistant gene, comprising ampicillin-resistant, neomycin-resistant, or tetracycline-resistent gene. Resistence to such antibiotic may, for example, indicate success of transfection or transformation of the desired construct into a host.

A "tag" comprises a sequence of extra nucleotides or the peptide transcript thereof, where a ligand can bind. Among other uses, tags serve as simple and efficient means to detect and purify the desired product, especially where little is known about the protein product of the foreign nucleic acid. Antibodies that recognize tags and purification columns containing ligands that bind to the tags are usually commercially-available. For example, a tag can be a segment of six histidines covalently linked together and positioned upstream or downstream of the foreign protein product; antibodies to six-histidine tags can be used to detect the foreign protein; commercially available nickel columns can be used to separate the foreign protein from the rest of the cellular lysate, thereby facilitating purification of the foreign protein.

Applicants have discovered that an isolated 5'-flanking segment of the murine CD-RAP gene (designated herein the "CD-RAP promoter"), when operably linked to a desired nucleic acid sequence, preferentially, and evidence shows, specifically, targets that nucleic acid sequence for expression in cartilage cells of the chondrocyte lineage and in mature chondrocytes. For example, transient transfection analysis was performed where various cell lines were transfected with CD-RAP promoter and a reporter gene luciferase. The promoter could drive expression of luciferase in mouse, rat, and human chondrocytes, but was inactive in fibroblasts and an osteoblast cell line. The CD-RAP flanking segment can be utilized to target expression of desired products in chondrosarcoma and cell lines derived therefrom, and mammary tumor cells and cell lines derived therefrom. Furthermore, the present invention contemplates that analogous CD-RAP promoters from other species, such as human, behave similarly to the murine CD-RAP promoter.

The nucleotide constructs containing the murine CD-RAP promoter segment isolated by applicants can be used for tissue-specific expression in the types of tissue cells described above in cells of other mammalian species, including rat, bovine and human. The complete sequence of the murine CD-RAP promoter/gene is set forth in FIG. 6. The 5'-flanking segment of the murine CD-RAP gene used in the nucleotide construct of the present invention is a segment of a size and sequence which is capable of targeting operably linked nucleic acid sequences for expression. Preferably, the segment comprises at least about the first 2.2 kb upstream from the translation start site of the murine CD-RAP gene, and most preferably, it comprises at least the positions from −2251 to −2068 upstream.

For most applications, the desired nucleic acid sequence to be operably linked to the CD-RAP promoter will preferably comprise a foreign nucleic acid sequence (i.e., a nucleic acid which does not express murine CD-RAP) which can be transcribed into RNA and may, in most applications, be translated into a peptide which carries out a preselected function in the cell which has been targeted for transformation. Thus, a great variety of foreign nucleic acid sequences can be operably linked to the murine CD-RAP promoter to create a nucleotide construct for cartilage-specific and/or chondrosarcoma/mammary tumor preferential expression. These comprise sequences which will produce antisense oligonucleotides for antisense therapy regimens, and those which will express antigenic proteins, growth factors, inhibitors, drugs and other proteins and polypeptides known to have utility for tissue-specific application by those skilled in this art. Such desired nucleic acid sequences may be combined and operably linked to the same or different murine CD-RAP promoter sequences, e.g., to include a reporter gene which will signal when a target cell has been transformed, or serve other purposes.

For certain purposes, e.g., transfection of cultured cell lines in vitro, the nucleotide constructs of the present invention are incorporated into plasmids, viral particles or other vectors using techniques well known in the art. See, e.g., Maniatis et al., Molecular Cloning: A Laboratory Manual, Cold Spring Harbor Laboratory, Cold Spring Harbor, N.Y. (2 d Ed. 1989), incorporated herein by reference. An example of the construction of a vector containing the CD-RAP promoter nucleotide construct using the placF expression vector is set forth below.

Transgenic animals, preferably mammals, containing the murine CD-RAP promoter nucleotide construct are also provided. Preferably, the transgenic animals of the present invention are capable of transmitting the nucleotide construct to their descendants. In particular, the creation of a transgenic mouse is illustrated below. For example, transgenic mice harboring various lengths of the mouse CD-RAP promoter linked to the *Escherichia coli* β-galactosidase gene (lacZ) were generated. The results indicate that the mouse CD-RAP promoter from −2251 to −2068 contains the transcriptional regulatory elements that are essential for the tissue-specific expression in vivo. Applicants have discovered and isolated the cis-acting elements that can target correct spatiotemporal expression in vivo and further defined the functional role of CD-RAP it embryonic development. Hence, specific in vivo expression of foreign nucleic acid operably linked to a CD-RAP promoter can be achieved with the present invention.

Thus, a method for the expression of a desired nucleic acid sequence in cartilage cells of the chondrocyte lineage or mature chondrocyte cells is provided by the present invention. Briefly, the method comprises the steps of transfecting the cells with a nucleotide construct containing a murine CD-RAP gene 5'-flanking segment capable of targeting cartilage-specific tissue for expression operably linked to a desired nucleic acid sequence to be expressed, and expressing the desired nucleic acid sequence. Preferably, a means is provided to select the transformed cells from those which have not been transformed. Illustratively, transformation can be confirmed by detecting β-galactosidase activity when the lacZ reporter gene is incorporated in the nucleotide construct, as described in the experimental section below.

Because of the selective expression targeted by the isolated murine CD-RAP promoter in chondrosarcoma cells and mammary tumor cells, the method of the invention may be employed following the same procedure described above to preferentially target expression of a desired nucleic acid sequence in chondrosarcoma cells and cell lines derived from chondrosarcoma cells and in mammary tumor cells and in cells lines derived from mammary tumor cells. The finding of CD-RAP in mammary buds suggests that CD-RAP may play a role in early breast development and later contribute to breast carcinogenesis. In the normal adult breast and lactating gland, no CD-RAP expression is observed (Lu et al., 1997). In our CD-RAP transgenic mice experiments, CD-RAP expression in mammary gland primordium was detected on day 11.5 p.c. The expression levels increased until day 13.5–14.5 of gestation and then diminished on day 16.5 p.c., suggesting that CD-RAP may play a role in the formation of mammary buds, but not in the later proliferation and differentiation into the mammary cord.

A further aspect of the present invention relates to applications of a transcription factor, preferably sox9, to alter expression of a CD-RAP promoter construct. For example, cotransfection of a recombinant sox9 and a CD-RAP promoter construct into a chrondrosarcoma cell line induces CD-RAP promoter activity as shown in FIG. 7. Therefore, using sox9, expression of various foreign nucleic acids operably linked to a CD-RAP promoter can be induced. In addition, the level of expression of the foreign nucleic acid can be controlled by the amount of recombinant sox9 introduced.

The following examples illustrate the invention, but are not to be taken as limiting the various aspects of the invention so illustrated.

EXAMPLES

Example 1

Production of Transgenic Mice
A. Construction of the Mouse CD-RAP Promoter-lacZ Fusion Gene The expression vector used was placF, which contains the lacZ reporter gene, followed by a sequence of the murine protamine gene that supplies an intron and a polyadenylation signal (Mercer et al., 1991). Three different lengths of the mouse CD-RAP promoter were generated by PCR amplification using a 3'-antisense primer that bound at −3 relative to the CD-RAP translational start site in conjunction with a 5'-sense primer that bound at various distances within the CD-RAP upstream flanking sequences. To facilitate subcloning of the amplified fragment, the sense primer contains a XbaI restriction site adaptor, and the antisense primer contains a SalI recognition site. After digestion with XbaI and SalI, the 2251 bp, 2068 bp, and 1427 bp of the promoter fragments were cloned into the polylinker regions of placF by standard recombinant techniques to generate three DNA constructs (2251lacZ, 2068lacZ, and 1427lacZ, respectively) as shown in FIG. 1.

B. Generation and Identification of Transgenic Mice

The DNA constructs were digested with XbaI and HindIII to release the inserts from their vector sequences. The enzymes cleaved right upstream of the mouse CD-RAP promoter and downstream of the polyadenylation signal. The fragments containing the 2251lacZ, 2068lacZ and 1427lacZ transgenes free of the vector sequences were isolated from agarose gel and the purified DNAs were microinjected into the pronuclei of fertilized eggs from B6SJL hybrid to generate transgenic mice, as described previously (Hogan et al., 1994). The surviving eggs were implanted into the pseudopregnant foster mothers. Founder mice were identified by PCR assays of the genomic DNA extracted from tail. The lacZ-specific primers used in PCR were as follows: sense, 5'-GCATCGAGCTGGGTAATAAGCGTTGGCAAT-3' SEQ ID NO: 2; antisense, 5'-GACACCAGACCAACTGGTAATGGTAGCGAC-3' SEQ ID NO: 3, which were expected to amplify an 822 bp fragment (Hanley and Merlie, 1991). Transgenic mouse lines were maintained by outbreeding with the B6SJL wild type mice. To analyze the temporal and spatial pattern of the β-galactosidase expression in the established lines, the positive founder or F1 were mated with the B6SJL wild type females and embryos were isolated at different days of gestation. The days of the vaginal plug was designated day 0.5 of gestation.

Example 2

Detection of Transgene Expression During Murine Development

A. Localization of Transcriptional Regulatory Elements

To assess the spatiotemporal expression pattern of transgenes, the β-galactosidase activity was detected in whole embryo as described (Bonnerot and Nicolas, 1993). Briefly, embryos were liberated from uterus and fixed in 4% paraformaldehyde at 4° C. for 20–40 min on a rocker. After overnight incubation at 30° C. in the staining solution with X-gal (5-bromo-4-chloro-3-indolyl-β-D-galactopyranoside; Sigma Chem. Co., St. Louis, Mo.), the positive embryos were washed in phosphate-buffered saline, photographed, and postfixed in 4% paraformaldehyde overnight.

Two of the five transgenic lines harboring the 2251lacZ exhibited detectable β-galactosidase activity with X-gal staining. The transgenic mice is maintained as described earlier which allows analysis of the transgene expression at different embryo stages. No variation in the pattern and the intensity of the transgene expression was observed in different embryos of the same established line and between these two positive transgenic lines.

A total of 13 transgenic founder mice carrying 2068lacZ were obtained. None of the offspring of these founders revealed any detectable β-galactosidase activity during the different embryonic stages. Similarly, no X-gal staining was observed in the embryos of a total of 10 transgenic founder animals harboring 1427lacZ which were generated from 43 embryos (Table I). These results indicate that the sequences between −2251 and −2068 of the mouse CD-RAP promoter contain the cis-acting elements necessary for tissue-specific expression. The promoter contains a TATA box and the binding sites for transcription factors such as Sp1, LEF-1, AP-2, and SOX9. The subsequent experiments were carried out using one of the two established transgenic lines carrying 2251lacZ and demonstrating positive X-gal staining.

B. Spatiotemporal Expression of A Transgene

To investigate the spatiotemporal expression pattern of transgene, the transgenic embryos were collected at days 10.5, 11.5, 12.5, 13.5, 15.5 and 16.5 of gestation by Cesarean section and whole mount-stained with X-gal. The earliest positive staining was observed in the third branchial arch at day 10.5 postconception (p.c.). The third branchial arch arteries give rise to the common carotid arteries in the region of the carotid body and carotid sinus. At day 11.5 p.c., 2251lacZ began to generate expression in cartilage of the developing bones including mandible and clavicle that is consistent with the results of in situ hybridization (Bosserhoff et al., 1997a). The proximal part of forelimb was also slightly stained at this stage which is correlated with the advent of the differentiation of limb buds (FIG. 2A). Interestingly, applicants also detected faint staining in mammary buds at this stage. Mammary ridge begins to appear on both sides of the ventral midline on day 11 p.c. in the normal female mouse development. Within each ridge, epithelial cells concentrate and form mammary buds. The epithelial cells proliferate rapidly immediately prior to birth, giving rise to the mammary cord. The transgene expression in mammary gland primordium continued throughout day 15.5 p.c. with the strongest expression observed at day 13.5 p.c. (FIGS. 2, A–D).

Figure 2B:
Figure 2C:
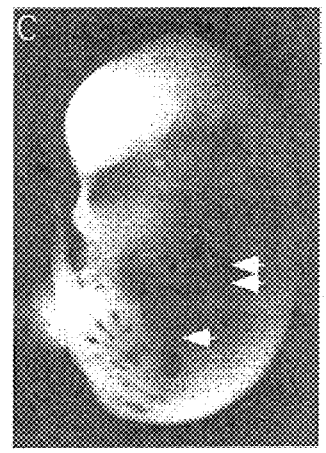
Figure 2D:
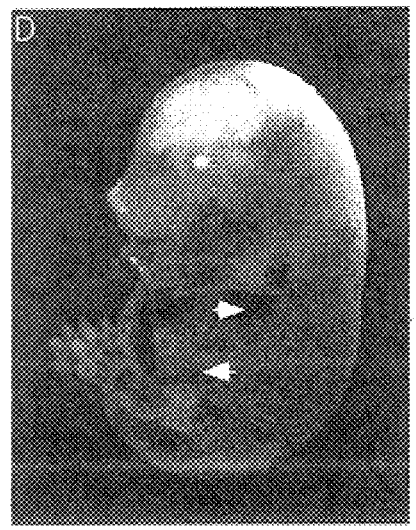
Figure 2E:

At day 12.5 p.c., the intensive X-gal staining was observed in the primordial cartilage of large diarthroses, including shoulder, elbow, knee, and ankle articulations, while faint staining was also seen in the cartilage anlages of long bones and phalanges in the limbs. The X-gal staining intensity in mammary gland primordium was increased (FIG. 2B). The transgene expression in cartilage became more evident at day 13.5 p.c. The vertebrate column, scapula, clavicle and nasal cartilage and several craniofacial structures were clearly stained with X-gal at day 13.5 p.c. (FIG. 3C). As the chondrogenesis proceeded to the proximal phalanges by day 15.5 p.c., the lacZ expression was still clearly detected in the distal cartilage and the proximal articulations, while the expression in mammary gland primordium was decreased (FIG. 2D). Applicants also detected X-gal staining on the tip of genital tubercle at this stage (data not shown). No staining in mammary gland primordium was observed at day 16.5 p.c. The transgene expression in cartilage remained almost the same intensity as that of day 15.5 embryo (FIG. 2E). No X-gal staining was detected in skin at anytime during the embryonic development. No detectable β-galactosidase activities were identified in osteogenic and bone cells, nor in neuroepithelium, periosteum, and perichondrium.

In summary, except the transient X-gal staining in mammary gland primordium and genital tubercle, the 2251lacZ directed the expression exclusively in almost all the cartilaginous tissues during the various mouse embryo stages, including both the axial and peripheral skeleton, the cartilage involved in endochondral ossification, and the cartilage that will not undergo ossification, such as nasal and articular cartilage. No expression was observed in other non-cartilaginous tissues such as somites, notochord, skin, heart, liver and kidney.

C. Histochemistry

For histological examination, the stained embryos were dehydrated in ethanol and embedded in paraffin. 5–10-μm thick sections were sliced on a microtome and countstained with eosin. Whole mount-staining demonstrates that the 2251 bp of the mouse CD-RAP promoter contains the cis-acting elements which are essential for generating lacZ expression in cartilaginous tissues and mammary gland primordium. To determine the nature of cells that conferred the μ-galactosidase activity, the stained transgenic embryos were sectioned and the tissue sections were countstained with eosin. Microscopic observation shows that all the epithelial cells in mammary buds were intensively stained from day 11.5 to 15.5 p.c. as observed in the whole mount embryo staining (FIGS. 3, A and B).

The transgene expression was also located in the chondrocytes of cartilage. As shown in FIG. 4A, X-gal staining was positive in chondrocytes of ribs and cartilaginous lung bronchi. No lacZ expression was detected in liver and kidney (FIG. 3A). Histological examination of the forelimb of day 15.5 p.c. reveals that 2251lacZ targeted strong expression mainly in proliferation chondrocytes, while the expression was reduced in hypertrophic chondrocytes (FIG. 4B). In adult animals, the transgene still generated lacZ expression in cartilage. FIG. 4C shows that the chondrocytes in cartilage surface of an 8-week knee joint section were clearly stained with X-gal. In contrast to type II procollagen, which is expressed transiently in certain non-chondrogenic tissues during embryogenesis and skeleton development, including somites, mesoenchymal and epithelial cells, notochord, heart and discrete areas of the brain (Sandell et al., 1991; Cheah et al., 1991; Sandell et al., 1994), no detectable lacZ expression was identified in these tissues, nor in kidney, muscle, neuroepithelium, periosteum, perichondrium, osteogenic and bone cells. The pattern of transgene expression is similar to that of the endogenous CD-RAP gene as applicants have shown by in situ hybridization (Bosserhoff et al., 1997a).

Example 3

Endogenous CD-RAP Expression
Immunohistochemistry

To examine the endogenous CD-RAP expression during the embryo development, applicants carried out the immunohistochemistry to localize CD-RAP. Antibodies against human recombinant CD-RAP/MIA were generated in rabbits by Boehringer-Mannheim, Penzburg, Germany. The X-gal staining was carried out overnight to identify the mammary gland before tissue sectioning. The paraffin-embedded tissues of 13.5-day-old embryos were employed for immunolocalization of CD-RAP. Immunohistochemistry was carried out using a DAKO LSAB 2-HRP Kit (Dako Corp., Carpinteria, Calif.) according to manufacturer's instructions. The primary antibodies against CD-RAP were used at a dilution of 1:500.

The endogenous CD-RAP expression in cartilage has been demonstrated before by in situ hybridization and immunohistochemistry (Bosserhoff et al., 1997a). However, no CD-RAP expression was detected in mammary buds by in situ hibridization. To examine the endogenous CD-RAP expression in mammary gland, an immunohistochemistry was performed to localize CD-RAP using a 13.5-day-old embryo. As shown in FIG. 5, CD-RAP was detected in the cytoplasm of epithelial cells in mammary buds. In addition, CD-RAP was observed in the cytoplasm of chondrocytes and the surrounding cartilage matrix. Applicants' transgene analysis has shown that CD-RAP is not only present in chondrocytes, but transiently expressed in mammary gland. These results demonstrate that the 2251lacZ transgene expression pattern is consistent with the endogenous CD-RAP expression.

Example 4

Induction of CD-RAP Promoter Construct by sox9

A. Construction of Mouse CD-RAP Promoter-Luciferase Fusion Gene

A 2251 bp of the mouse CD-RAP promoter was amplified by polymerase chain reaction (PCR). The PCR fragment and a promoterless luciferase expression vector pGL3-Basic were digested separately with SmaI and HindIII. The purified CD-RAP promoter fragment and vector were ligated.

B. Luciferase Assay of Cotransfected sox9 and CD-RAP Promoter Construct

Two micrograms of the sox9 expression plasmid in pcDMA vector is cotransfected with 0.5 µg of the CD-RAP promoter construct and 0.5 µg of an internal control plasmid pCMV-βgal into RCS (rat chondrosarcoma) cells using calcium phospate mammalian cell transfection kit. Glycerol shock was performed 4 h later for 3 minutes with 15% glycerol. The cells were further cultured for 42–48 h in standard culture medium. The lysate was analyzed for luciferase activity with a Turner TD 20e luminometer using Promega luciferase assay reagent. The β-galactosidase activity was measured with 50 µl of the lysate using the colormetric assay as described by the manufacturer. The luciferase activities were normalized to the β-galactosidase value. Luciferase activity of each cotransfection is compared to the luciferase activity of a control transfection, consisting of a CD-RAP promoter construct and a vector without a sox9 gene. FIG. 7 represents average values of CD-RAP promoter activities from three independently transfected cultures from one representative experiment. The luciferase value of the control (without sox9) was set at 1.

C. Luciferase Assay of Truncated sox9 Inhibition of CD-RAP Promoter Activity

Different amounts (0 µg, 1 µg, and 5 µg) of wild-type sox9 or truncated sox9 were cotransfected with lug of CD-RAP promoter construct into RCS cells as described in above. Three independent transfection experiments were performed. Data presented in FIG. 8 are average values of the three transfections. The activity of the wild-type construct was set at 100 .

Applicants have demonstrated that SOX9 is capable of stimulating the CD-RAP promoter activity through a SOX9 binding site. When sox9 is able to bind to the sox consensus sequence, i.e. to the wild-type sox consensus sequence, luciferase activity increases, indicating increased CD-RAP promoter activity. See FIG. 7. Applicants' studies, however, reveal that sox9 cannot activate CD-RAP in nonchondrogenic cells, which is consistent with prior understanding (Lefebvre and de Crombrugghe, 1998). As mentioned earlier, transgenic mice harboring DNA constructs 1427lacZ and 2068lacZ, both containing the AP-2 and SOX9 motifs in their promoters, failed to generate any detectable β-galactosidase activity in tissues, while the construct 2251lacZ directed the correct temporal and spatial expression in cartilage. These experiments indicate that the fragment from −2251 to −2068 contains the transcriptional regulatory domains which are essential for the generation of cartilage expression, but other transcription factors besides AP-2 and SOX9 are critical in the transcriptional activation of CD-RAP gene.

Applicants' data also show that increasing amounts of wild-type sox9 increases CD-RAP promoter activity. With increasing amounts of truncated sox9, on the other hand, CD-RAP promoter activity is inhibited. See FIG. 8.

In view of the above, it will be seen that the several objects of the invention are achieved and other advantageous results attained.

References

Bell, D. M., K. K. H. Leung, S. C. Wheatley, L. J. Ng, S. Zhou, K. W. Ling, M. H. Sham, P. Koopman, P. P. L. Tam, and K. S. E. Cheah. 1997. SOX9 directly regulates the type-II collagen gene. Nat. Genet. 16:174–178.

Blesch, A., A. K. Bosserhoff, R. Apfel, C. Behl, B. Hessdoerfer, A. Schmitt, P. Jachimczak, F. Lottspeich, R. Buettner, and U. Bogdahn. 1994. Cloning of a novel malignant melanoma-derived growth-regulatory protein, MIA. Cancer Res. 54:5695–5701.

Bonnerot, C., and J.-F. Nicolas. 1993. Application of lacZ gene fusions to postimplantation development. Methods Enzymol. 225:451–469.

Bosserhoff, A. K., R. Hein, U. Bogdahn, and R. Buettner. 1996. Structure and promoter analysis of the gene encoding the human melanoma-inhibiting protein MIA. J. Biol. Chem. 271:490–495.

Bosserhoff, A. K., S. Kondo, M. Moser, U. H. Dietz, N. G. Copeland, D. J. Gilbert, N. A. Jenkins, R. Buettner, and L. J. Sandell. 1997a. Mouse CD-RAP/MIA Gene: structure, chromosomal localization, and expression in cartilage and chondrosarcoma. Dev. Dyn. 208:516–525.

Bosserhoff, A. K., M. Kaufmann, B. Kaluza, I. Bartke, H. Zirngibl, R. Hein, W. Stolz, and R. Buettner. 1997b. Melanoma-inhibiting activity, a novel serum marker for progression of malignant melanoma. Cancer Res. 57:31493153.

Bosserhoff, A. K., R. Hein, F. Wach, and R. Buettner. 1997c. Function of MIA in metastasis of malignant melanoma. Proceedings of the American Association for Cancer Research 38:290.

Bridgewater, L. C., V. Lefebvre, and B. de Crombrugghe. 1998. Chondrocyte-specific enhancer elements in the Col1la2 gene resemble the Col2 al tissue-specific enhancer. J. Biol. Chem. 273:14998–15006.

Cheah, K. S. E., E. T. Lau, P. K. C. Au, and P. P. L. Tam. 1991. Expression of the mouse α1(II) collagen genes is not restricted to cartilage during development. Development 111:945–953.

Davis, R. L., H. Weintraub, and A. B. Lassar. 1987. Expression of a single transfected cDNA converts fibroblasts to myoblasts. Cell 51:987–1000.

Dietz, U. H., and L. J. Sandell. 1996. Cloning of a retinoic acid-sensitive mRNA expressed in cartilage and during chondrogenesis. J. Biol. Chem. 271:3311–3316.

Ducy, P., R. Zhang, V. Geoffroy, A. L. Ridall, and G. Karsenty. 1997. Osf2/Cbfa1: a transcriptional activator of osteoblast differentiation. Cell 89:747–754.

Foster, J. W., M. A. Dominguez-Steglich, S. Guioli, C. Kwok, P. A. Weller, M. Stevanovic, J. Weissenbach, S. Mansour, I. D. Young, P. N. Goodfellow, J. D. Brook, and A. J. Schafer. 1994. Campomelic dysplasia and autosomal sex reversal caused by mutations in an SRY-related gene. Nature 372:525–530.

Gilbert, S. F. 1994. Developmental biology, 4 th ed. Sinauer Associates, Inc., Massachusetts.

Grosschedl, R., K. Giese, and J. Pagel. 1994. HMG domain proteins: architectural elements in the assembly of nucleoprotein structures. Trends Genet. 10:94–100.

Hanley, T., and J. P. Merlie. 1991. Transgene detection in unpurifed mouse tail DNA by polymerase chain reaction. Biotechniques 10:56.

Hogan, B., R. Beddington, F. Costantini, and E. Lacy. 1994. Manipulating the mouse embryo: a laboratory manual. 2nd ed. Cold Spring Harbor Laboratory Press, New York.

Horton, W., T. Miyashita, K. Kohno, J. R. Hassell, and Y. Yamada. 1987. Identification of a phenotype-specific enhancer in the first intron of the rat collagen II gene. Proc. Natl. Acad. Sci. USA. 84:8864–8868.

Kim, J. B., and B. M. Spiegelman. 1996. ADD1/SREBP1 promotes adipocyte differentiation and gene expression linked to fatty acid metabolism. Genes Dev. 10:1096–1107.

Kondo, S., S. H. Cha, A. Oganesian, Y. Zhu, W. F. Xie, and L. J. Sandell. 1998. Regulation and function of CD-RAP, a new cartilage-specific protein. Orthop. Trans. 21:28.

Lefebvre, V., W. Huang, V. R. Harley, P. N. Goodfellow, and B. de Crombrugghe. 1997. SOX9 is a potent activator of the chondrocyte-specific enhancer of the proα1(II) collagen gene. Mol. Cell. Biol. 17:2336–2346.

Lefebvre, V., and B. de Crombrugghe. 1998. Toward understanding SOX9 function in chondrocyte differentiation. Matrix Biol. 16:529–540.

Lu, J., H. Pei, M. Kaeck, and H. J. Thompson. 1997. Gene expression changes associated with chemically induced rat mammary carcinogenesis. Mol. Carcinogenesis 20:204–215.

Mercer, E. H., G. W. Hoyle, R. P. Kapur, R. L. Brinster, and R. D. Palmiter. 1991. The dopamine β-hydroxylase gene promoter directs expression of E. coli lacZ to sympathetic and other neurons in adult transgenic mice. Neuron 7:703716.

Molkentin, J. D., B. L. Black, J. F. Martin, and E. N. Olson. 1995. Cooperative activation of muscle gene expression by MEF2 and myogenic bHLH proteins. Cell 83:1125–1136.

Ng, L.-J., S. Wheatly, G. E. O. Muscat, J. Conway-Campbell, J. Bowles, E. Wright, D. M. Bell, P. P. L. Tam, K. S. E. Cheah, and P. Koopman. 1997. SOX9 binds DNA, activates transcription, and coexpresses with type II collagen during chondrogenesis in the mouse. Dev. Biol. 183:108–121.

Ryan, M. C., M. Sieraski, and L. J. Sandell. 1990. The human type II procollagen gene: identification of an additional protein-coding domain and location of potential regulatory sequences in the promoter and first intron. Genomics 8:41–48.

Sandell, L. J., N. Morris, J. R. Robbin, and M. B. Goldring. 1991. Alternatively spliced type II procollagen mRNAs define distinct populations of cells during vertebral development: differential expression of the amino-propeptide. J. Cell Biol. 114:1307–1319.

Sandell, L. J., A. M. Nalin, and R. A. Reife. 1994. Alternative splice form of type II procollagen mRNA (IIA) is predominant in skeletal precursors and non-cartilaginous tissues during early mouse development. Dev. Dyn. 199:129–140.

Savagner, P., T. Miyashita, and Y. Yamada. 1990. Two silencers regulate the tissue-specific expression of the collagen II gene. J. Biol. Chem. 265:6669–6674.

Schorle, H., P. Meier, M. Buchert, R. Jaenisch, and P. J. Mitchell. 1996. Transcription factor AP-2 essential for cranial closure and craniofacial development. Nature 381:235–238.

Süadbeck, P., M. L. Schmitz, P. A. Baeuerle, and G. Scherer. 1996. Sex reversal by loss of the C-terminal transactivation domain of human SOX9. Nat. Genet. 13:230–232.

Tontonoz, P., E. Hu, and B. M. Spiegelman. 1994. Stimulation of adipogenesis in fibroblasts by PPARγ2, a lipid-activated transcription factor. Cell 79:1147–1156.

van Groningen, J. J. M., H. P. J. Bloemers, and G. W. M. Swart. 1995. Identification of melanoma inhibitory activity and other differentially expressed messenger RNAs in human melanoma cell lines with different metastatic capacity by messenger RNA differential display. Cancer Res. 55:6237–6243.

Wright, E., M. R. Hargrave, J. Christiansen, L. Cooper, J. Kun, T. Evans, U. Gangadharan, A. Greenfield, and P. Koopman. 1995. The Sry-related gene Sox9 is expressed during chondrogenesis in mouse embryos. Nat. Genet. 9:15–20.

Xie, W.-F., S. Kondo, and L. J. Sandell. 1998. Regulation of the mouse cartilage-derived retinoic acid-sensitive protein gene by the transcription factor AP-2. J. Biol. Chem. 273:5026–5032.

Xie, W.-F., S. Sakano, V. Lefebvre, and L. J. Sandell. 1999. Trans-activation of the Mouse Cartilage-Derived Retinoic Acid-Sensitive Protein Gene by Sox9. J. Bone Miner. Res. 14:757–763.

Yoshioka, H., K. Iyama, K. Inoguchi, M. Khaleduzzaman, Y. Ninomiya, and F. Ramirez. 1995. Developmental pattern of expression of the mouse α1(XI) collagen gene (Col11a1). Dev. Dyn. 204:41–47.

Zhang, J., S. Hagopian-Donaldson, G. Serbedzija, J. Elsemore, D. Plehn-Dujowich, A. P. McMahon, R. A. Flavell, and T. Williams. 1996. Neural tube, skeletal and body wall defects in mice lacking transcription factor AP-2. Nature 381:238–241.

Zhao, Q., H. Eberspaecher, V.-Lefebvre, and B. de Crombrugghe. 1997. Parallel expression of Sox9 and Col2a1 in cells undergoing chondrogenesis. Dev. Dyn. 209:377–386.

Zhou, G., V. Lefebvre, Z. Zhang, H. Eberspaecher, and B. de Crombrugghe. 1998. Three high mobility group-like sequences within a 48-base pair enhancer of the Col2a1 gene are required for cartilage-specific expression in vivo. J. Biol. Chem. 273:14989–14997.

What is claimed:

1. A method for the expression of a desired nucleic acid sequence encoding a desired protein in a cartilage cell of the chondrocyte lineage or a mature chondrocyte cell comprising the step of transfecting the cell with a nucleotide construct comprising the murine CD-RAP gene promoter of SEQ ID NO:1 operably linked to said desired nucleic acid sequence, wherein said promoter targets said desired nucleic acid sequence for expression in said cartilage cell of the chondrocyte lineage or mature chondrocyte cell, and wherein said nucleic acid sequence is expressed in said cartilage cell of the chondrocyte lineage or mature chondrocyte cell.

2. A method for the expression of a desired nucleic acid sequence encoding a desired protein in chondrosarcoma cells or cell lines derived from chondrosarcoma cells comprising the step of transfecting the cells with a nucleotide construct comprising the murine CD-RAP gene promoter of SEQ ID NO:1 operably linked to said desired nucleic acid sequence , wherein said promoter targets said desired nucleic acid sequence for expression in said chondrosarcoma cells or cell lines, and wherein said nucleic acid sequence is expressed in said chondrosarcoma cells or cell lines.

3. A method for the expression of a desired nucleic acid sequence encoding a desired protein in mammary tumor cells or cell lines derived from mammary tumor cells comprising the step of transfecting the cells with a nucleotide construct comprising the murine CD-RAP gene promoter of SEQ ID NO:1 operably linked to said desired nucleic acid sequence encoding a desired protein, wherein said promoter targets said desired nucleic acid sequence for expression in said mammary tumor cells or cell lines; and wherein said nucleic acid sequence is expressed in said mammary tumor cells or cell lines.

4. A nucleotide construct comprising the murine CD-RAP gene promoter of SEQ ID NO:1 operably linked to a desired nucleic acid sequence, wherein the desired nucleic acid sequence encodes a desired protein, and wherein the expression by the promoter is increased by the wild-type sox9 transcription factor.

5. A vector comprising a nucleotide construct, wherein said nucleotide construct comprises the murine CD-RAP gene promoter of SEQ ID NO:1 operably linked to a desired nucleic acid sequence, wherein the desired nucleic acid sequence encodes a desired protein, and wherein the expression by the promoter is increased by the wild-type sox9 transcription factor.

6. The vector of claim 5, wherein the desired nucleic acid sequence construct encodes a reporter protein.

7. The vector of claim 5, wherein the murine CD-RAP gene promoter comprises about the first 2200 nucleotides of SEQ ID NO: 1 usptream from the translation start site.

8. The vector of claim 5, wherein the murine CD-RAP gene promoter comprises the nucleotides 1 through 184 of SEQ ID NO: 1.

9. The vector of claim 6, wherein the reporter gene is a lacZ reporter gene.

10. The method of claim 1, wherein the CD-RAP promoter of SEQ ID NO:1 comprises about 2200 nucleotides upstream from the translation site of the CD-RAP gene of SEQ ID NO:1.

11. The method of claim 1, further comprising determining the level of expression of the desired nucleic acid sequence.

12. The method of claim 2, wherein the CD-RAP promoter of SEQ ID NO:1 comprises about 2200 nucleotides upstream from the translation site of the CD-RAP gene of SEQ ID NO:1.

13. The method of claim 2, further comprising determining the level of expression of the desired nucleic acid sequence.

14. The method of claim 3, wherein the CD-RAP promoter of SEQ ID NO:1 comprises about 2200 nucleotides upstream from the translation site of the CD-RAP gene of SEQ ID NO:1.

15. The method of claim 3, further comprising determining the level of expression of the desired nucleic acid sequence.

16. A method for the targeted expression of a desired protein in a cell of the chondrocyte lineage or a mammary tumor cell comprising transfecting a nucleotide construct comprising the murine CD-RAP gene promoter of SEQ ID NO:1 operably linked to a desired nucleic acid sequence, wherein the desired nucleic acid sequence encodes a desired protein, and wherein the expression by the promoter is increased by the wild-type sox9 transcription factor, in said cell of the chondrocyte lineage or a mammary tumor cell, wherein the desired protein is expressed in said cell of the chondrocyte lineage or a mammary tumor cell, thereby expressing said nucleic acid sequence in said cell of the chondrocyte lineage or a mammary tumor cell.

17. The method of claim 16, wherein the CD-RAP promoter of SEQ ID NO:1 comprises about 2200 nucleotides upstream from the translation site of the CD-RAP gene of SEQ ID NO:1.

18. The method of claim 16, further comprising determining the level of expression of the desired nucleic acid sequence.

19. The method of claim 16, wherein the desired nucleic acid sequence construct encodes a reporter protein.

20. The method of claim 16, wherein the murine CD-RAP gene promoter comprises about the first 2200 nucleotides of SEQ ID NO:1 usptream from the translation start site.

21. The method of claim 16, wherein the murine CD-RAP gene promoter comprises nucleotides 1 through 184 of SEQ ID NO:1.

22. The method of claim 19, wherein the reporter protein is expressed by a lacZ reporter gene.

* * * * *

SEQUENCE LISTING

<160> NUMBER OF SEQ ID NOS: 3

<210> SEQ ID NO 1
<211> LENGTH: 3831
<212> TYPE: DNA
<213> ORGANISM: Mus musculus;
<220> FEATURE:
<221> NAME/KEY: misc_feature
<222> LOCATION: (3591)..(3591)

```
<223> OTHER INFORMATION: n = a, t, c or g
<220> FEATURE:
<221> NAME/KEY: misc_feature
<222> LOCATION: (3598)..(3598)
<223> OTHER INFORMATION: a = a, t, c or g
<220> FEATURE:
<221> NAME/KEY: misc_feature
<222> LOCATION: (3624)..(3624)
<223> OTHER INFORMATION: n = a, t, c or g
<220> FEATURE:
<221> NAME/KEY: nisc_feature
<222> LOCATION: (3790)..(3790)
<223> OTHER INFORMATION: n = a, t, c or g
<220> FEATURE:
<221> NAME/KEY: misc_feature
<222> LOCATION: (3805)..(3805)
<223> OTHER INFORMATION: n = a, t, c or g
<220> FEATURE:
<221> NAME/KEY: misc_feature
<222> LOCATION: (3821)..(3821)
<223> OTHER INFORMATION: n = a, t, c or g

<400> SEQUENCE: 1
ccaaggagtc taccaataga gctacattta gtccctatg tattagttag ttgtctccca      60
gaggccttca gattttcatg ccttgaatct tcacagtgcc aagatttgaa actagtattt     120
acagtaaaat atctactgcc caaagaaaca ctttgatgta ttctaaattg ggaaattcaa     180
aacatgagaa caacatgcta cctcatggtc tctgctacca gcttcattta tttaccaact    240
tgtgtctaaa acttctcaag gaaatcacct cctacactta ttttacagtg gtcttactgt    300
tttagttttt gtggttctgg gcattgaacc cagggctttg tacatactag acaaagctca    360
gtcctgggcc cctgacatat attttagtta taaattatca tacattattt tttggcttgg    420
gaattgaacc caagattatc aggcattcaa ccactatgtt cctgtcctgt tgctatgaag    480
agacaccaga actaaagtaa attaaaggca gagcatttac tagaggtctt gcttatagtt    540
gaagagaatc agttcgtggt gattatgaca gcatggcagc aggcaggcat gatgccaaag    600
caatagctga gagcttaaac ctggcaaaga tgaggcagtg aaaaggagag gaaatgtgtg    660
ggggtgtggt gggggtctg gcttggactt ttttttttcat taaaaatttt tttattagat    720
attttctttta tttacatttt aaatattatc cctttccta gtttcccctc tgaaaatccc    780
ctctcccctc cccatggct tgagcttttg aaacttaaaa gctcacaccc agtgacagaa    840
ctctaccaac aaggtcatct gccaaccttc ctaaacagtt ccacctactg ggaaccaaac    900
attcacatat actagcctat tgggaccacc ttattcaaac tataaccatt aagctatagt    960
ttcagcctca gtctgttgat tgcatccttg tgaggtcact aaacatgctc tttgggcctc   1020
tgttccttgc acgtctgttc atggactgct ccttctaaga ggcatgtcag gtcagataac   1080
agtgatacta agaaaccctg aaataaatct tttttttccc ttcctggttc agttaccata   1140
gacatacatt ctttagctca atttctttgt gaactgggct tgtcagggct actcctgagg   1200
caattcagac catccctgat atacatat atgatttta cacatgcata tatatgtatg     1260
tgtatatata catacataca tatatatagt atatacacat atatattttg tgtgggtgta   1320
catacacaca catgcatatg atttgctggt gcatgcctta cccacgtttg gaaaggcaga   1380
ggcaggttga tctcttaaga gtttgaggcc agtctggtct ttatagggag ttccaggcca   1440
gccagggctg tgcagtagta gatcggtgtc tcaagaaaaa agagtgggct ggaaagatgg   1500
ctcagcggtt aagagcagag cacgagtggg tcttccagat gacccaggtt tgattcctag   1560
cacctagctc tgtagctcca gttccagaag actcaagacc ctcttctggc ctttaaaaat   1620
accaggcaca catgcagtac tcagacatac atgcagcagt tgtttgcttt cattgctttc   1680
```

-continued

```
tttatagatg agtgggttga agctcataag ctagaatagc ttagcttcta gtgaggaagt    1740
aagcctgtga atgtgcacag tgagccaggt gggacagtgc ctagcctgag gccagacgtt    1800
gagtgtttgc tcagtacctg ggaaccctgg ctgtggctgc taatcaaaga actgccttgt    1860
tctcagacct cagcacagga aattccaggg tggttttcta tactggctcc tctagcttgg    1920
tctctggagg gtccaggtac ctaaaacgac ttgaaggtgg aatcagatag tccagcctgc    1980
ctatctgcgt ctctagttat ccaggggGtg atcgctactt ggaattgcct gaattgcttt    2040
gggctcgagt aggcattttc tttggcccat agcccttacc ctctctctaa aatggtactg    2100
gctggagaac aaccttgggg agtgggtgag ggtgaaattt ggtttggggc ggagacagga    2160
tcgagaacac aggtttcctt gatattcagc ctggaaggag ggcaggagga gcccagagac    2220
ctcgttcttc acttggtcat tctcagtcca tgatggtgtg gtccccagtg ctccttggca    2280
tcgtcgtctt gtctgttttt tcagggccta gcagggctga tcgagctatg cccaagctgg    2340
ctgactggaa gctgtgtgcg gacgaggaat gcagccgtaa gagtcaggga acaagggaag    2400
ggggctgaag gcttggactg ctagtctgtt ttgcagttgc tgtcatttcc ttctccctcc    2460
ccagatccta tctccatggc tgtggccctc caggactacg tggcccctga ttgccgcttc    2520
ttgactatat atagggggcca agtggtgtat gtcttctcca agttgaaggg ccgtgggcgc    2580
cttttctggg gaggcagtgt gagtcttcaa aaagtgataa tgggaagggt gtgggtttg    2640
tttgggtttg taaagccttg ttttccatat gaagggaaga tttgggggga ggggaaaacg    2700
agatttgggg gaaggaagga catttttatta cttattgcat tttttttttt ttctttagaa    2760
attacagaga agcttagcgc caaagctctt tttcataccc gggatacaac agtgaacaaa    2820
ggggtagagg caggcaacca gcaagccatc aaaagtggca gcaaacatga cattgtgagg    2880
attagttgta gtggcaacat tctatccatg agcaaatggc atttaagctg agattcaagt    2940
aagagggaag attgtacaca ggcgttcagc aagcataagt gccgtttccc cagatggact    3000
tttaacttct tctccaggtt cagggaggtt actatggaga cctggcagcc cgcctgggct    3060
atttccccag tagcattgtc cgggaggacc tgactctgaa acctggcaaa attgatatga    3120
agaccgatgt gagtgtcttg ggggtggagg tgggagtagg atgatagttc ctttatttgc    3180
ttacctgttt atgagaagta attattttttg ttgttggtat gtacccaagc tggcctcaaa    3240
atcactagcc tccagtttca gcctcctgag ggctgctgag tttacaggcc ctgcccagtg    3300
ctgagtgatc tctaattggg aaatggcaga gggtgcagta ctggaagcta atgtgttcat    3360
ttctgggtga tcaaacctag tccttgcagc tataactttg ttagaaccac taggcgcatt    3420
gcaatgtcat cactggttgg ttttctattt actcttttttc agcaatggga tttctactgc    3480
cagtgagctc agcctaccgc tatccctgca gttacccttc cggctctatg caaatacagc    3540
agccaatggc aaactatttg tctctttggt ttttggggtt gggtgggtat ntgcaaanaa    3600
tgtttcacgg gtttctgaat atanccaatt aatgccctga atgttgtaac gtcagtggct    3660
actaggcaaa atttcacttt gcaagcccctt tgctccaagg taaggtttgg gaccccccaag    3720
caaggggggta aacagtacaa tatatgtacg ctttcctctc ttttaaaggg agttgaatca    3780
ttggtatgan ccaatagatc ccganaagcg catagaacgt ncagttttttt t    3831
```

<210> SEQ ID NO 2
<211> LENGTH: 30
<212> TYPE: DNA
<213> ORGANISM: Artificial Sequence
<220> FEATURE:

-continued

```
<221> NAME/KEY: misc_feature
<222> LOCATION: (1)..(30)
<223> OTHER INFORMATION: lacZ-specific primer used in PCR

<400> SEQUENCE: 2
gcatcgagct gggtaataag cgttggcaat                                30

<210> SEQ ID NO 3
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: lacZ-specific primer used in PCR

<400> SEQUENCE: 3
gacaccagac caactggtaa tggtagcgac                                30
```